US00PP30015P3

(12) United States Plant Patent
Larse

(10) Patent No.: US PP30,015 P3
(45) Date of Patent: Dec. 25, 2018

(54) STRAWBERRY PLANT NAMED 'MAGELLAN'

(50) Latin Name: ***Fragaria* x *ananassa***
Varietal Denomination: Magellan (a.k.a. 108789)

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 15/731,552

(22) Filed: Jun. 28, 2017

(65) Prior Publication Data

US 2018/0235125 P1 Aug. 16, 2018

Related U.S. Application Data

(60) Provisional application No. 62/355,575, filed on Jun. 28, 2016.

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
See application file for complete search history.

*Primary Examiner* — Annette H Para
(74) *Attorney, Agent, or Firm* — Cooley LLP

(57) ABSTRACT

The present invention provides a new and distinct strawberry plant designated as 'Magellan' (a.k.a. '108789').

3 Drawing Sheets

Latin name of the genus and species: *Fragaria* x *ananassa.*

Varietal denomination: 'Magellan' (a.k.a. '108789').

BACKGROUND OF THE INVENTION

The present invention relates to a new and distinct strawberry plant designated as 'Magellan' (a.k.a. '108789'). 'Magellan' is a short-day strawberry plant.

'Magellan' (a.k.a. '108789') is the result of a controlled-cross between a female parent cultivar designated '107705' (unpatented, proprietary cultivar) and a male parent cultivar designated '106861' (unpatented, proprietary cultivar) made by the Inventor and was first fruited in Watsonville, Calif. growing fields. Following selection and during testing, the plant was originally designated '108789' and subsequently named 'Magellan'.

This new strawberry plant was asexually reproduced via runners (stolons) by the inventor at Watsonville, Calif. Asexual propagules from the original source have been tested in Watsonville growing fields and to a limited extent, grower fields in high elevation. The properties of this new strawberry plant were found to be transmissible by such asexual reproduction. This new strawberry plant is stable and reproduce true to type in successive generations of asexual reproduction.

BRIEF SUMMARY OF THE INVENTION

This invention relates to a new and distinctive strawberry plant designated as 'Magellan'. This strawberry plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits and photographs in combination distinguish strawberry plant 'Magellan' from known strawberry varieties. In addition, this new strawberry plant was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The fruit produced by each new cultivar is attractive and of excellent quality.

DESCRIPTION OF THE DRAWINGS

The accompanying color photographs depict various characteristics of the cultivars as nearly true as possible to make color reproductions.

DETAILED DESCRIPTION OF THE INVENTION

'Magellan' (a.k.a. '108789')

Figure 1:
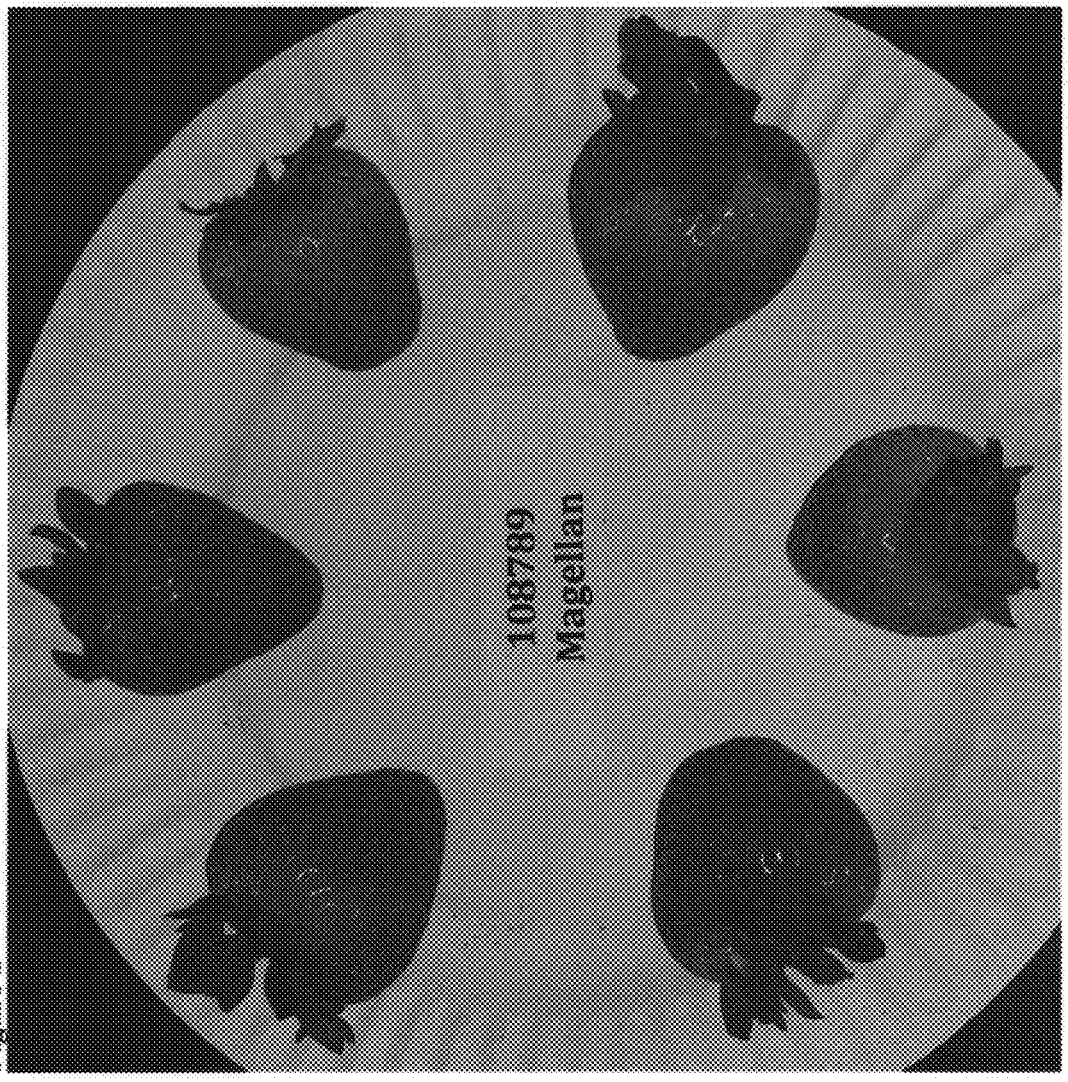
FIG. 1 shows fruits of 'Magellan'.
Figure 2:
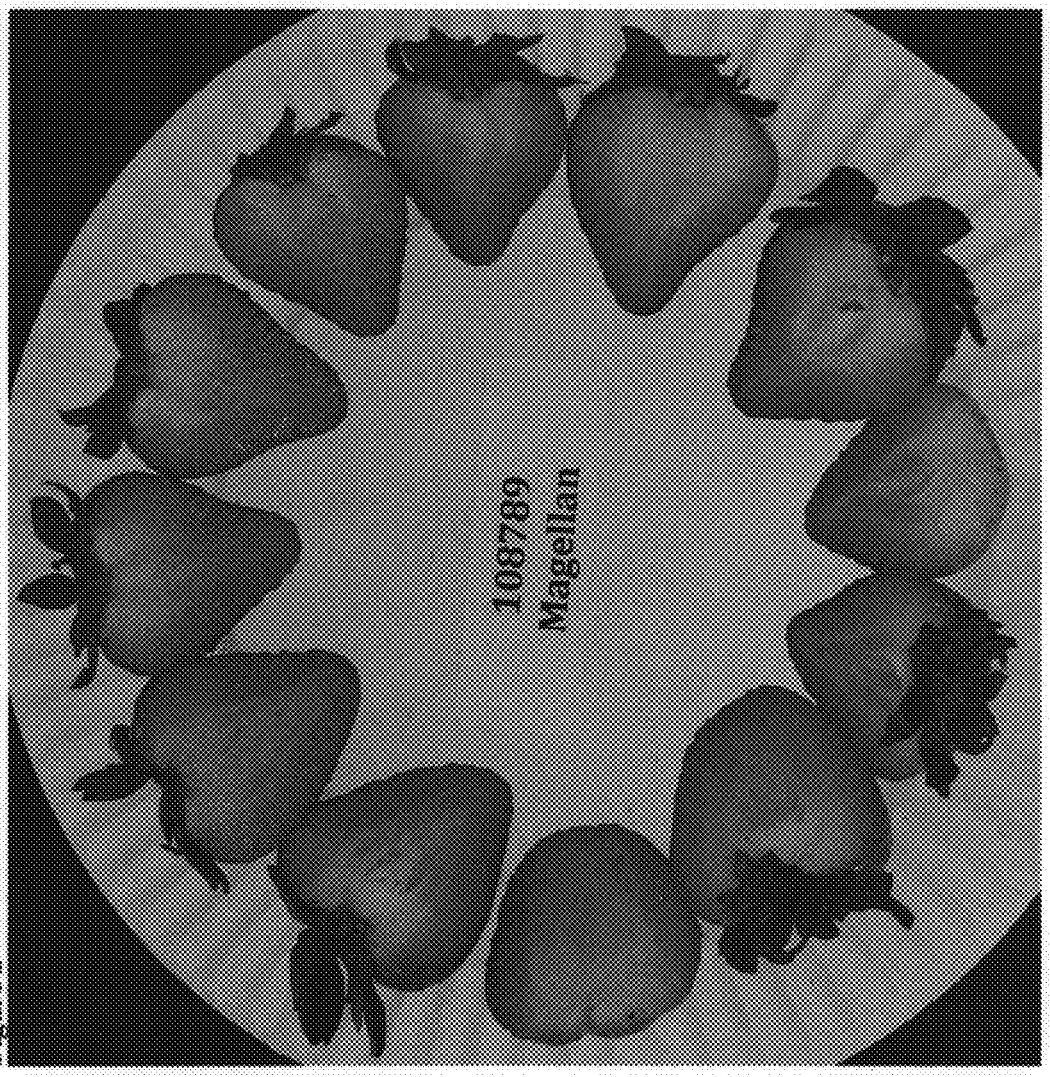
FIG. 2 shows sliced fruits of 'Magellan'.
Figure 3:
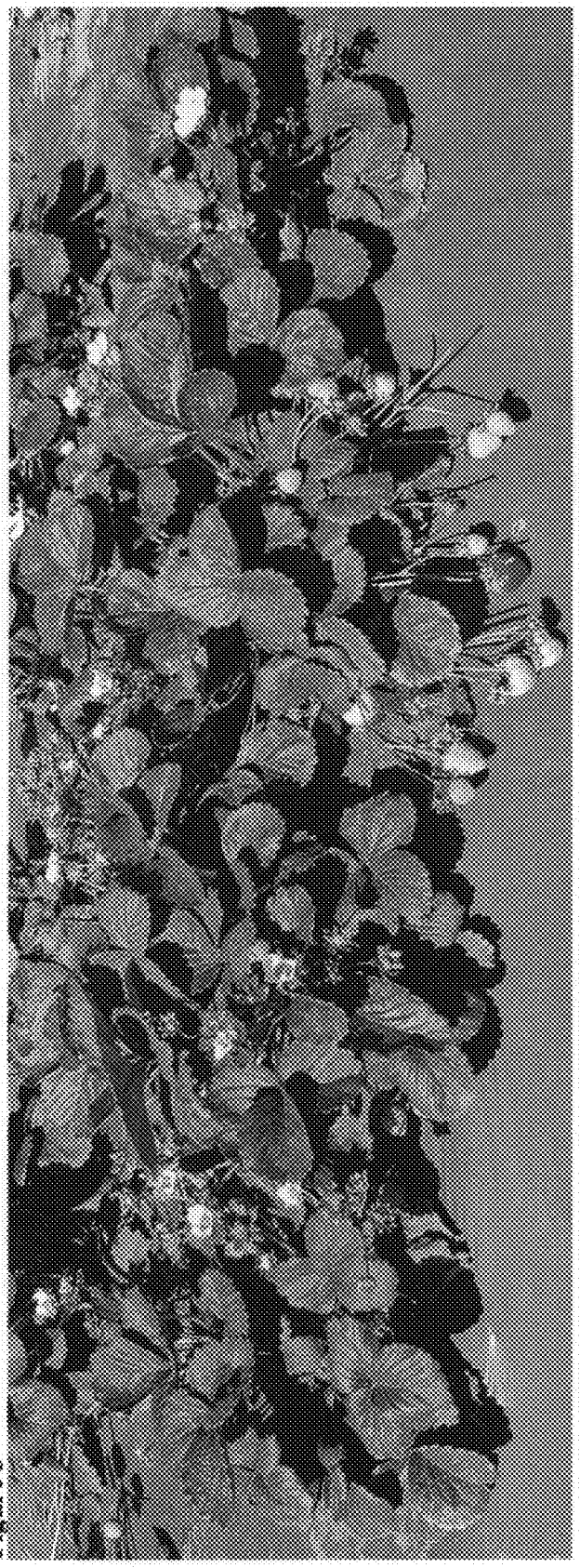
FIG. 3 shows 'Magellan' plants.

This invention relates to a new and distinctive short-day type strawberry cultivar designated as 'Magellan'. It is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits in combination distinguish strawberry plant 'Magellan' from the known strawberry plants. Plants for the botanical measurements in the present application were grown as annuals. In the following description, color references are made to The Royal Horticultural Society Colour Chart, 1995 Edition, except where general terms of ordinary dictionary significance are used.

The detailed botanical description in Table 1 was observed when the plants were 33 weeks after planting.

'Magellan' has not been observed under all possible environmental conditions, and the phenotype may vary significantly with variations in environment. The following observations, measurements, and comparisons describe this plant as grown under normal conditions in Watsonville, Calif. unless otherwise noted.

TABLE 1

| Magellen | | |
|---|---|---|
| CharType | Characteristic | Magellan |
| General | Plant Habit | annual |
| | Plant Growth Habit | upright |
| | Plant Height | 24 cm |
| | Plant Width | 29 cm |
| | Plant Width-Crown | 3 cm |
| | Density of foliage, vigor | medium |
| | Plant vigor | moderate to high |
| Leaf | Terminal leaflet width (mm) | 79 |
| | Terminal leaflet length (mm) | 82 |
| | No. teeth/terminal leaflet: | 19 |
| | Shape of the terminal leaflet base | rounded |
| | Shape of terminal leaflet in cross-section | concave |
| | Margin description of the terminal | serrate to crenate |
| | Color of upper side of leaves | 137A |
| | Color of lower side of leaves | 139C |
| | Leaf blistering | weak |
| | Leaf glossiness | weak |
| Limbs | Petiole length (cm) | 13 |
| | Petiole diameter (mm) | 3.89 |
| | Petiole color | 145B |
| | Petiolule length (mm) | 6 |
| | Petiolule diameter (mm) | 3.89 |
| | Attitude of hairs on petiole and pedicel | upwards |
| | Stipule pubescence | medium to heavy |
| | Stipule length (cm) | 5 |
| | Stipule size | large |
| | Stipule width (cm) | 1.2 |
| | Stipule anthocyanin | present |
| | Stipule color (color code) | 145A |
| | Pedicel color (color code) | 145B |
| | Peduncle length (cm) | 27 |
| | Peduncle size | medium to large |
| | Peduncle attitude | erect |
| | Peduncle pubescence, attitude of hairs | Medium, upwards |
| Inflorescence | Inflorescence position relative to foliage | above |
| | Flower arrangement of petals | touching |
| | Petal length (cm) | 1.5 |
| | Petal width (cm) | 1.5 |
| | Petal number per flower | 6 |
| | Upper Petal color | 155C |
| | Lower Petal color | 157B |
| | Calyx diameter (cm) | 3.9 |
| | Corolla diameter (cm) | 3.5 |
| | Sepal length (cm) | 1.6 |
| | Sepal width (cm) | 0.4 |
| | Time of flowering (50% of plants in bloom) | March |
| | Shape of stigma | capitate |

TABLE 1-continued

| Magellen | | |
|---|---|---|
| CharType | Characteristic | Magellan |
| | Color of stigma | 12A |
| | Length of style (mm) | 2 |
| | Color of style | 4A |
| | Color of the ovary | 145B |
| | Length of the stamens (mm) | 5 |
| | Number of stamen | 25 |
| | Anther color | 12A |
| | Shape of anther | dorsifixed |
| | Size of anther | medium |
| | Amount of pollen | moderate |
| | Color of pollen | 4A |
| | Color of filament | 2C |
| | Length of filament (mm) | 4 |
| | Number of flowers per truss | 2 to 7 |
| Stolon | Stolon number | 3 |
| | Stolon anthocyanin | 166A |
| | Widest diameter of stolon At leaf attachment (mm) | 4.41 |
| | Stolon color | 145B |
| Fruit | Number of fruit per truss | 2 to 5 |
| | Fruit length (cm) | 4.2 |
| | Fruit width (cm) | 4.1 |
| | Fruit skin color | 53A to 45A |
| | Fruit flesh color excluding core | 44A |
| | Fruit core length (cm) | 3.4 |
| | Fruit core width (cm) | 1.8 |
| | Fruit core color | 41A |
| | Fruit weight (g) | 26.8 |
| | Predominant fruit shape | short wedge to conic |
| | Shape difference between primary & secondary fruits | Similar shape |
| | Width of band without of achenes | medium |
| | Fruit glossiness | medium to strong |
| | Position of achenes | |
| | Achene color | 145B |
| | Achenes per fruit | 438 |
| | Achene weight (g) | 0.26 |
| | Position of calyx | even to inserted |
| | level of adherence of calyx | strong |
| | Color of calyx | 137A |
| | Firmness of flesh | firm |
| | Evenness of flesh color | nearly even |
| | Sweetness (brix) | 9 |
| | pH | 3.27 |
| | Yield (g per plant per season) | 2675 |

When 'Magellan' is compared to the proprietary female parent (107705), the mean fruit width of 'Magellan' at the widest latitudinal measure is higher than that of the female parent. 'Magellan' fruit height is shorter than that of the female parent. 'Magellan' has a lower fruit dimension ratio (height/width) compared to the female parent. The fruit shape of 'Magellan' is symmetric conic, while the fruit shape of the female parent is conic. In terms of mean fruit yield between weeks 22 and 28 after planting, 'Magellan' is higher than the female parent.

When 'Magellan' is compared to the proprietary male parent (106861), the fruits of 'Magellan' are softer compared to the fruits of the male parent as measured by using a Wagner force gauge. 'Magellan' has a lower fruit dimension ratio (height/width) compared to the male parent. The fruit shape of 'Magellan' is symmetric conic, while the fruit shape of the male parent is conic. In terms of mean fruit yield between weeks 22 and 28 after planting, 'Magellan' is much higher than the male parent.

When 'Magellan' is compared to the check variety 'Albion' (U.S. Plant Pat. No. 16,228), the fruit dimension ratio (height/width) of 'Magellan' is lower than 'Albion', which confirms that 'Albion' has a longer conic fruit than the relatively round shape of 'Magellan'. The petiole of 'Albion' is slightly thicker than that of 'Magellan'. In terms of plant shape, 'Albion' was observed to spread or somewhat oblate while 'Magellan' was observed to be roundish. In terms of canopy foliage, 'Magellan' is denser and has higher cull rate than 'Albion', which makes it more difficult to harvest 'Magellan' than 'Albion'. The fruits of 'Magellan' are less susceptible to bruising than that of 'Albion'. 'Magellan' has a greater fruit yield than 'Albion' between weeks 22 and 28 after planting.

TABLE 2

Comparison of fruit features of 'Magellan' with the proprietary male and female parents

| HYBRID ID | HYBRID NAME | FRUIT WIDTH (mm) | FRUIT HEIGHT (mm) | FRUIT RATIO (Height/Width) |
|---|---|---|---|---|
| 106861 | Male Parent | 43.33 | 49.67 | 1.15 |
| 107705 | Female Parent | 36.50 | 44.25 | 1.21 |
| 108789 | Magellan | 39.96 | 42.98 | 1.08 |

TABLE 2-continued

Comparison of fruit features of 'Magellan' with the proprietary male and female parents

| HYBRID ID | FRUIT SHAPE* | HARDNESS (newtons) | Yield (g/clone) |
|---|---|---|---|
| 106861 | 7 | 9.42 | 405 |
| 107705 | 7 | N/A | 1061 |
| 108789 | 6 | 8.79 | 1143 |

*Fruit shape: 1. Oblate; 2. Globose; 3. Fan Lobes; 4. Necked; 5. Short wedge; 6. Symmetric conic; 7. Conic; 8. Long conic; 9. Long wedge

TABLE 3

Comparison of fruit features between 'Magellan' and the check variety

| HYBRID ID | HYBRID NAME | FRUIT WIDTH (mm) | FRUIT HEIGHT (mm) | FRUIT RATIO (Height/Width) |
|---|---|---|---|---|
| Check Variety | Albion (U.S. Plant Pat. No. 16,228) | 41.62 | 51.96 | 1.25 |
| 108789 | Magellan | 39.96 | 42.98 | 1.08 |

| HYBRID ID | FRUIT SHAPE* | HARDNESS (newtons) | Yield (g/clone) |
|---|---|---|---|
| Check Variety | 7 | 8.68 | 892 |
| 108789 | 6 | 8.79 | 1143 |

*Fruit shape: 1. Oblate; 2. Globose; 3. Fan Lobes; 4. Necked; 5. Short wedge; 6. Symmetric conic; 7. Conic; 8. Long conic; 9. Long wedge

The invention claimed is:

1. A new and distinct cultivar of strawberry plant named 'Magellan' substantially as shown and described herein.

* * * * *